(12) United States Patent
Cohen et al.

(10) Patent No.: US 7,931,589 B2
(45) Date of Patent: Apr. 26, 2011

(54) SURGICAL RETRACTOR DEVICE AND RELATED METHODS

(75) Inventors: Dan S. Cohen, Miami Beach, FL (US); Nicholas J. Bender, Budd Lake, NJ (US); Oliver Buchert, Wallington, NJ (US); Rui J. Ferreira, Livingston, NJ (US)

(73) Assignee: EBI, LLC, Parsippany, NJ (US)

( * ) Notice: Subject to any disclaimer, the term of this patent is extended or adjusted under 35 U.S.C. 154(b) by 564 days.

(21) Appl. No.: 11/558,095

(22) Filed: Nov. 9, 2006

(65) Prior Publication Data
US 2008/0114209 A1 May 15, 2008

(51) Int. Cl.
*A61B 1/32* (2006.01)
(52) U.S. Cl. .......................... 600/210; 600/225; 600/231
(58) Field of Classification Search ........... 600/201–246
See application file for complete search history.

(56) References Cited

U.S. PATENT DOCUMENTS

| | | | |
|---|---|---|---|
| 4,610,243 A | 9/1986 | Ray | |
| 4,926,849 A | 5/1990 | Downey | |
| 5,351,680 A | 10/1994 | Jung | |
| 5,512,038 A | 4/1996 | O'Neal et al. | |
| 5,616,117 A | 4/1997 | Dinkler et al. | |
| 5,728,046 A | 3/1998 | Mayer et al. | |
| 5,795,291 A | 8/1998 | Koros et al. | |
| 5,813,978 A | 9/1998 | Jako | |
| 5,828,139 A | 10/1998 | Slater | |
| 5,882,298 A | 3/1999 | Sharratt | |
| 5,908,382 A * | 6/1999 | Koros et al. | 600/232 |
| 5,944,658 A * | 8/1999 | Koros et al. | 600/232 |
| D415,274 S | 10/1999 | Koros et al. | |
| 5,993,385 A | 11/1999 | Johnston et al. | |
| D442,687 S | 5/2001 | Schulz | |
| 6,224,545 B1 | 5/2001 | Cocchia et al. | |
| 6,416,467 B1 | 7/2002 | McMillin et al. | |
| D475,975 S | 6/2003 | Fox | |
| 6,616,605 B2 | 9/2003 | Wright et al. | |
| 6,712,795 B1 | 3/2004 | Cohen | |
| 6,869,398 B2 | 3/2005 | Obenchain et al. | |
| 6,945,933 B2 | 9/2005 | Branch et al. | |
| 7,261,688 B2 * | 8/2007 | Smith et al. | 600/210 |
| D568,471 S | 5/2008 | Engler | |
| D575,396 S | 8/2008 | Wu | |

(Continued)

FOREIGN PATENT DOCUMENTS

DE 201 19 971 U1 3/2002

(Continued)

OTHER PUBLICATIONS

PCT Invitation to Pay Additional Fees mailed May 13, 2008 including a partial international search as an annex, for PCT/US2007/023708.

(Continued)

*Primary Examiner* — Eduardo C Robert
*Assistant Examiner* — Christina Negrelli
(74) *Attorney, Agent, or Firm* — Harness, Dickey

(57) ABSTRACT

A surgical retractor device. The surgical retractor device includes a frame having an outer frame member and an inner frame member coupled to the outer frame member for relative movement about a frame pivot axis, and a frame driver operable to rotate the outer frame member relative to the inner frame member about the frame pivot axis.

37 Claims, 9 Drawing Sheets

U.S. PATENT DOCUMENTS

| | | |
|---|---|---|
| D589,145 S | 3/2009 | Miller |
| 2004/0176665 A1 | 9/2004 | Branch et al. |
| 2004/0215199 A1 | 10/2004 | Zinkel |
| 2005/0192485 A1 | 9/2005 | Branch et al. |
| 2005/0277812 A1 | 12/2005 | Myles |
| 2006/0052672 A1 | 3/2006 | Landry et al. |
| 2007/0073111 A1* | 3/2007 | Bass .................... 600/215 |
| 2007/0100212 A1 | 5/2007 | Pimenta et al. |
| 2007/0293729 A1 | 12/2007 | Grey et al. |
| 2008/0033251 A1 | 2/2008 | Araghi |
| 2008/0183046 A1 | 7/2008 | Boucher et al. |
| 2009/0018399 A1 | 1/2009 | Martinelli et al. |
| 2009/0069635 A1* | 3/2009 | Gephart et al. ............ 600/224 |
| 2009/0203969 A1 | 8/2009 | Cohen et al. |

FOREIGN PATENT DOCUMENTS

| | | |
|---|---|---|
| EP | 0 143 124 A | 6/1985 |
| EP | 1435219 | 7/2004 |
| WO | 2005/016131 A | 2/2005 |
| WO | 2006/042241 A | 4/2006 |

OTHER PUBLICATIONS

Partial European Search Report dated Jan. 7, 2010 for Application No. EP 09 01 3262.

* cited by examiner

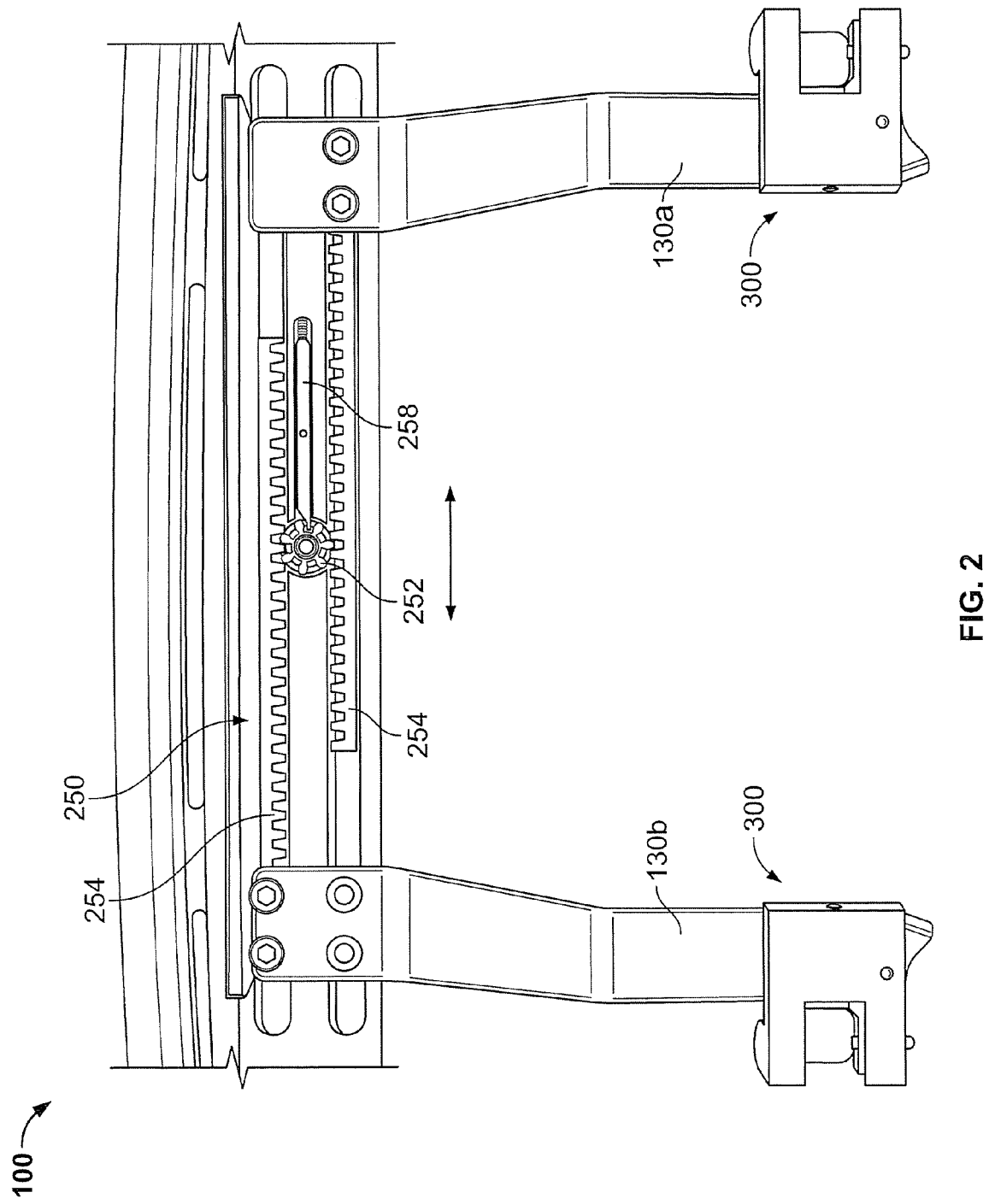

SURGICAL RETRACTOR DEVICE AND RELATED METHODS

INTRODUCTION

Various devices and associated methods are known for providing surgical access to portions of the human body. Such devices include, for example, forceps, dilators and retractors.

Continuing concern with reducing trauma, infection risk, and patient recovery time, encourages the development of instruments that may help reduce the invasiveness of surgical procedures. The present teachings provide such a surgical retractor device and associated methods for providing access to portions of the body.

SUMMARY

The present teachings provide a surgical retractor device. The surgical retractor device includes a frame having an outer frame member and an inner frame member coupled to the outer frame member for relative movement about a frame pivot axis, and a frame driver operable to rotate the outer frame member relative to the inner frame member about the frame pivot axis.

The present teachings also provide a surgical retractor device including a frame, a modular arm, and an arm connector releasably and self-lockingly coupling the modular arm to the frame, the arm connector allowing rotational motion of the modular arm relative to an axis of the frame.

The present teachings further provide a surgical retractor device for retracting a surgical opening of a patient. The surgical retractor device includes a generally U-shaped first frame member, the U-shaped first frame member defined by first and second end portions interconnected by an intermediate portion, a first quick engagement formation defined by the first end portion, at least one retractor arm coupled to the intermediate portion and movable in translation relative to the intermediate portion, and a modular arm coupled to the first quick engagement formation, the first modular arm rotatable relative to the first end portion.

The present teachings further provide a method of retracting a surgical opening of a patient. The method includes positioning a retractor having a frame relative to the surgical opening, pivoting a first frame member relative to a second frame member about a frame pivot axis, and inserting first and second retractor blades coupled to the frame into the surgical opening.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a partial bottom view of an exemplary retractor device according to the present teachings shown with a partial cut-away view of an distraction driver;

DESCRIPTION OF VARIOUS ASPECTS

The following description is merely exemplary in nature and is in no way intended to limit the invention, its application, or uses. The present teachings can be used for various surgical procedures in which access to portions of the body is desired, such as, for example, various orthopedic procedures, including anterior, posterior, or lateral spine surgeries. Furthermore, the present teachings can be used for retracting soft tissue, such as retracting open a small incision, and generally for maneuvering and aligning various implants and instruments through a limited area, such as, for example, in minimally invasive procedures.

Figure 1:
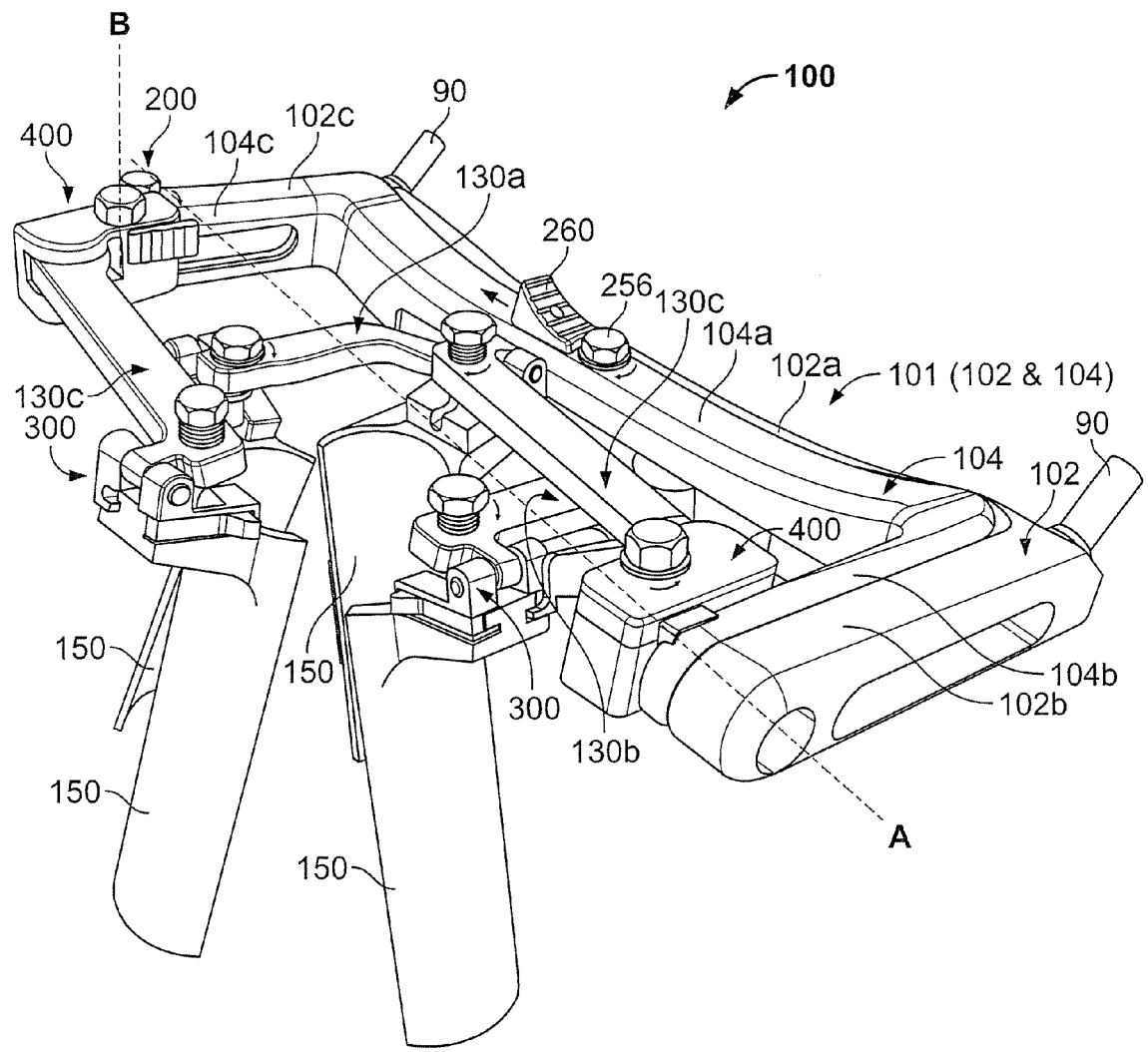
FIG. 1 is a perspective view of an exemplary retractor device according to the present teachings.

Referring to FIG. 1, an exemplary surgical retractor device according to the present teachings is illustrated and generally identified at reference character 100. The retractor device 100 can be shaped to fit the contour of the human body and as such the retractor device 100 can be flat, concave, convex, faceted, or any combination thereof. The retractor device 100 can include a frame 101 comprising an outer frame member 102, and an inner frame member 104 coupled to the outer frame member 102 by pivot pins or other linking elements 106, for pivotable motion about a frame pivot axis A. The outer frame member 102 can include a center or intermediate portion 102*a* and first and second end portions 102*b*, 102*c* arranged to generally define a U-like shape. Similarly, the inner frame member 104 can include an intermediate portion 104*a* and first and second end portions 104*b*, 104*c* arranged to generally define a U-like shape. The frame 101 can also include mounting stems 90 for connecting the frame 101 with a surgical table or other surgical structure in a known manner. The intermediate portions 102*a*, 104*a* of the frame 101 can have a convex or otherwise shaped lower surface for following the contour of the patient's anatomy. The frame 101 can also include various slots or windows for reducing weight, improving visualization and manipulation of the frame and related tools.

The outer and inner frame members 102, 104 can be pivotably coupled at the distal ends of their respective first end portions 102*b*, 104*b* and second end portions 102*c*, 104*c* in a nested-like configuration such that their respective intermediate portions 102*a*, 104*a* are adjacent to each other, and similarly, their respective first end portions 102*b*, 104*b*, and their respective second end portions 102*c*, 104*c*, are also adjacent to each other. The nested-like arrangement of the outer and inner frame members 102, 104 and their U-like shapes can provide free space for instrumentation and can reduce occlusion.

Figure 3A:
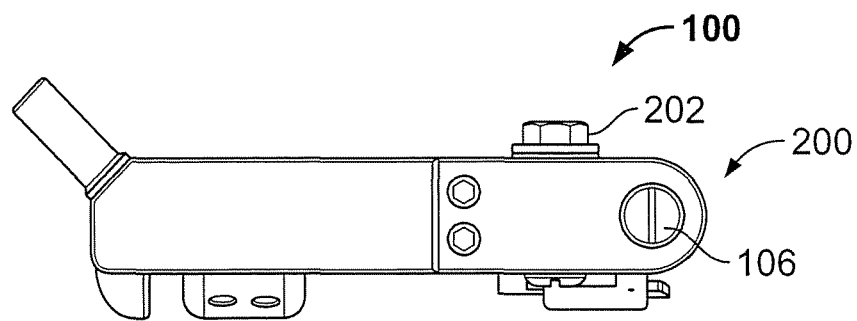
FIGS. 3A-3C are side views of an exemplary retractor device according to the present teachings with first and second frames shown in three different configurations.
Figure 3B:
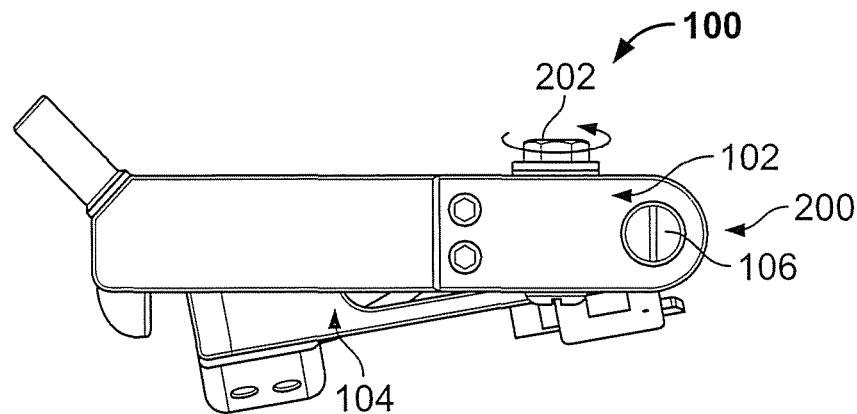
Figure 3C:
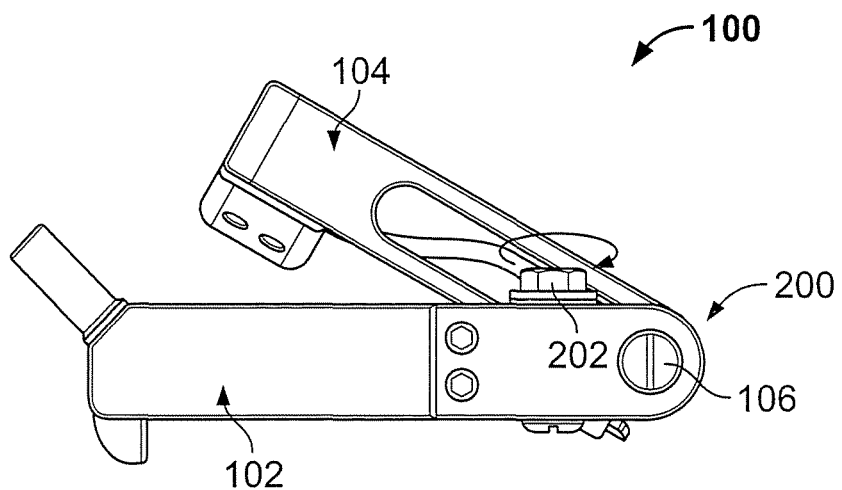
Figure 5:
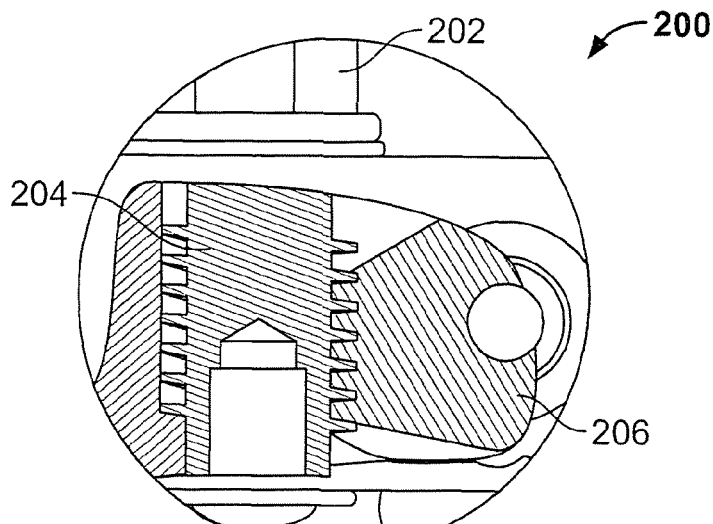
FIG. 5 is an enlarged sectional view of Detail A of FIG. 4.

Referring to FIG. 3A, the outer and inner frame members 102, 104 are shown in a neutral position in which the outer and inner frame members 102, 104 are substantially coplanar. A frame driver 200, shown in FIG. 5, can be actuated using a frame actuator 202. Rotating the actuator 202 in opposite directions can cause the inner frame member 104 to angle downward or upward relative to the outer frame member 102 in a continuous, non-incremental motion, as shown in FIGS. 3B and 3C. The frame driver 200 can be a gear-type driver, including, for example, a worm drive 204, and a gear 206 engaged to the worm drive 204 and connected to the linking element 106. Rotating the actuator 202 causes the worm drive 204 to rotate, driving the gear 206 and pivoting the inner frame member 104 relative to the outer frame member 102. The outer and inner frame members 102, 104 are held in the relative position reached when rotation of the actuator 202 ceases through the teeth meshing of the worm drive 204 and the gear 206.

Figure 7:
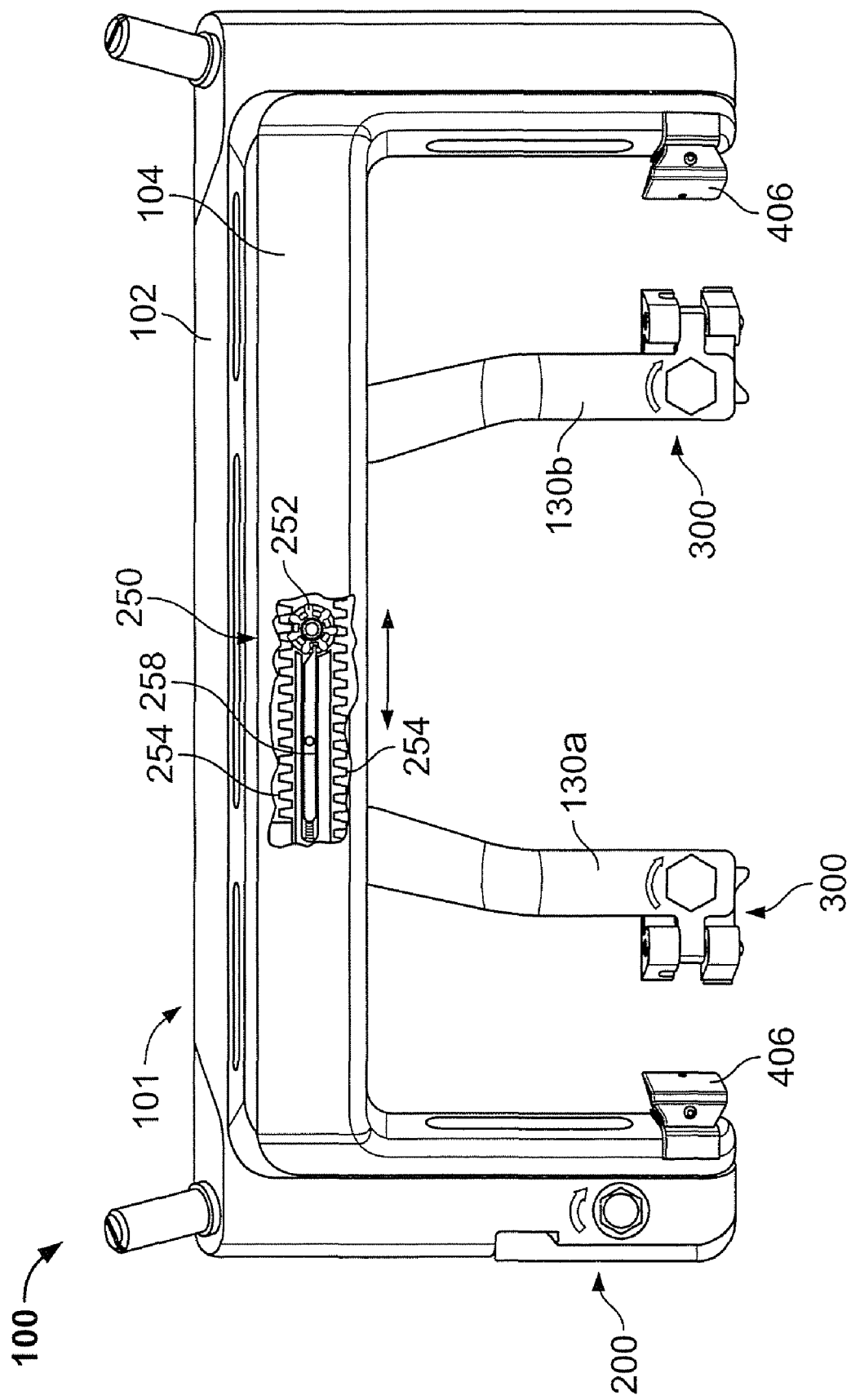
FIG. 7 a perspective top view of FIG. 4 shown with a partial cut-away view of a frame.

Referring to FIGS. 1, 2, 4, and 7, the retractor device 100 can include first and second retractor arms 130a, 130b movably connected at their proximal ends to the intermediate portion 104a of the inner frame member 104. A distraction or linear driver 250 can be used to drive the first and second retractor arms 130a, 130b closer together or further apart for distraction in a linear/translational motion, as shown in FIG. 7. The distraction driver 250 can include a pinion 252 that engages geared racks 254 coupled to the retractor arms 130a, 130b. Rotating the pinion 252 with a distraction actuator 256 drives the racks 254 to move the retractor arms 130a, 130b relative to one another. The first and second retractor arms 130a, 130b can move, for example, simultaneously from a center position outwardly away from each other, and inwardly toward each other. The actuator 256 can be, for example, a hex head attached to the pinion 252. A biased stopper 258 can be used to prevent motion of the first and second retractor arms 130a, 130b. The stopper 258 can be moved to a release position against bias by a moving a release element 260 connected to the stopper 258. In other applications, it may be desirable to only move one of the retractor arms 130a or 130b relative to the frame 101.

Figure 4:
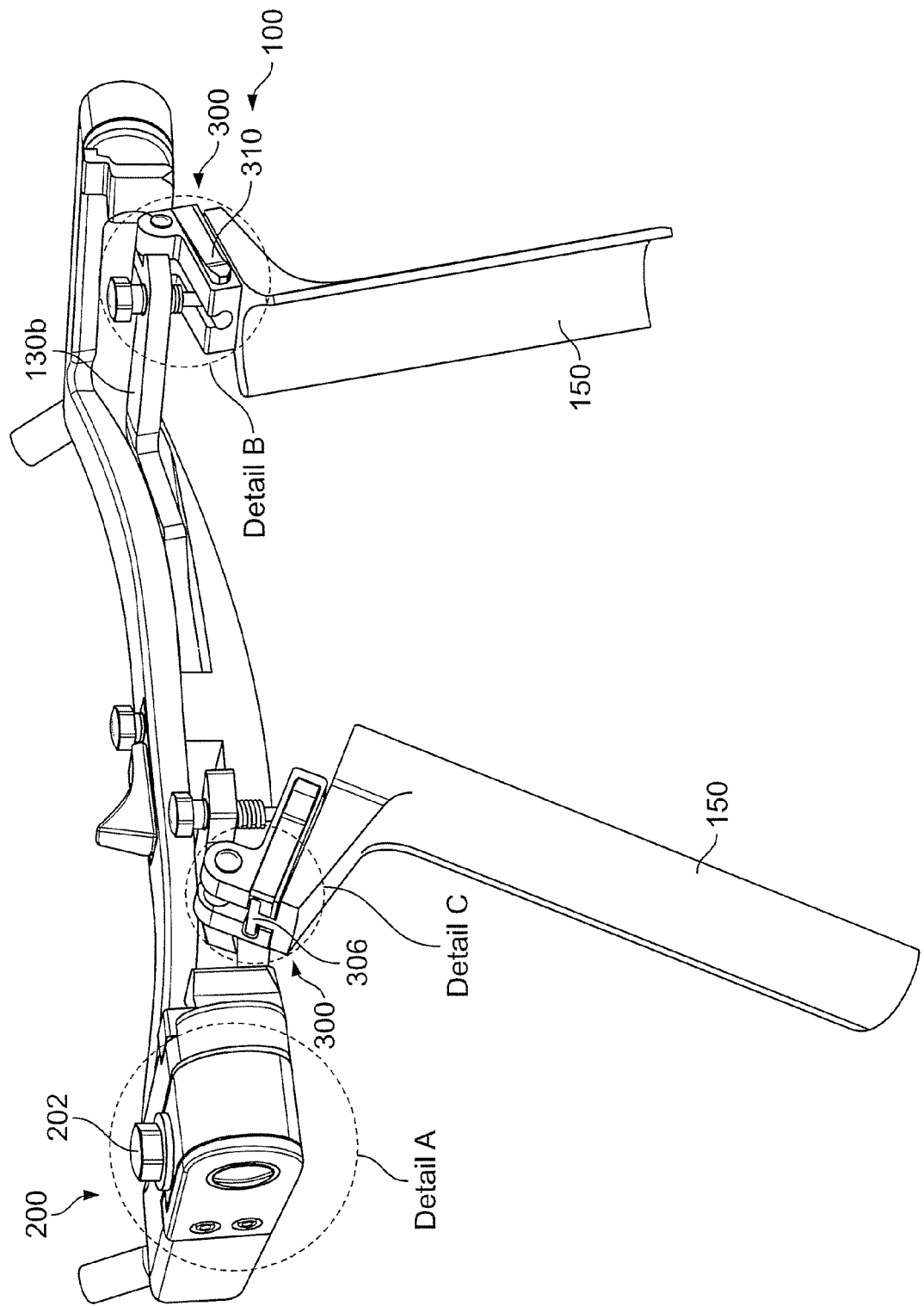
FIG. 4 is a perspective view of an exemplary retractor device according to the present teachings shown with two retractor blades.
Figure 6:
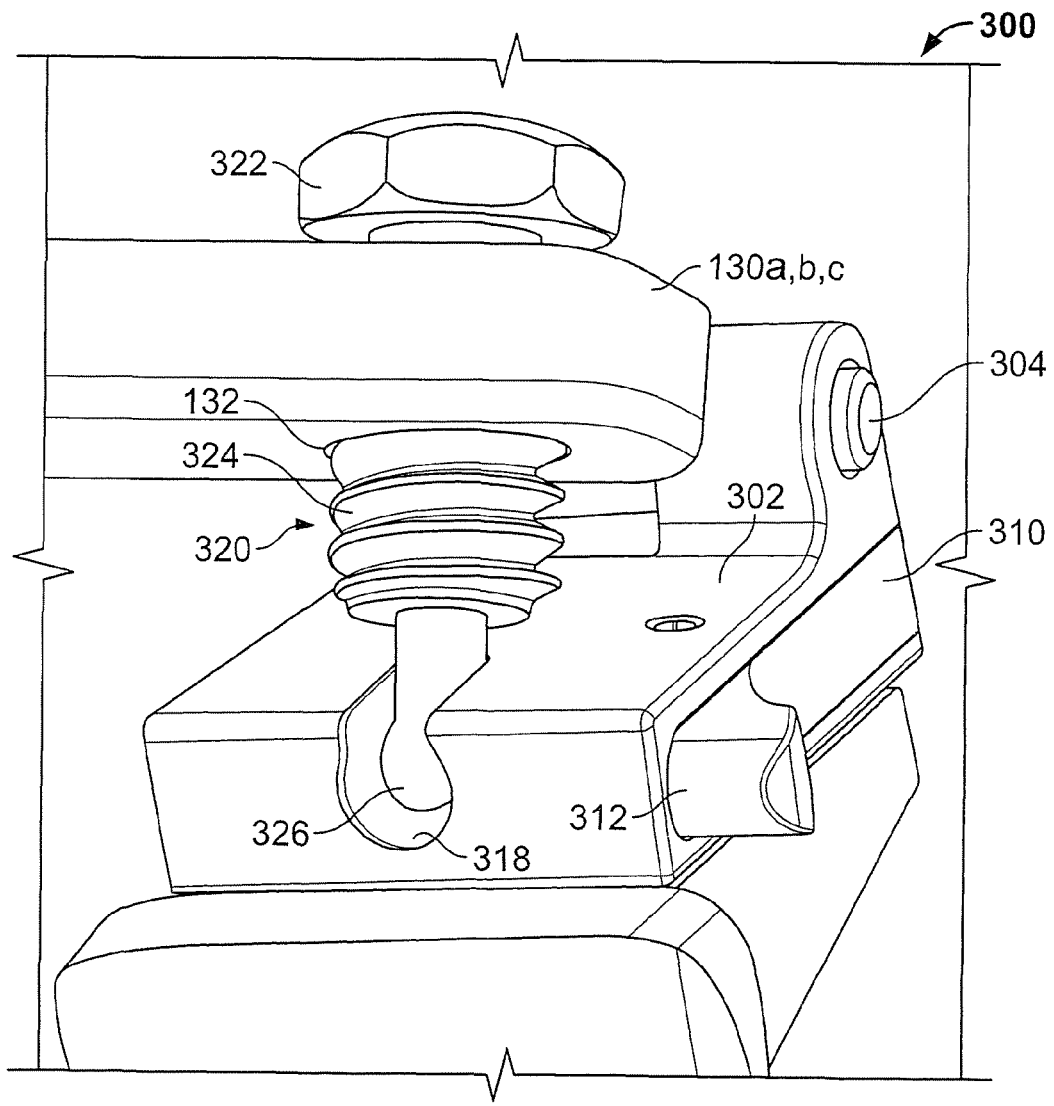
FIG. 6 is an enlarged view of Detail B of FIG. 4.
Figure 8:
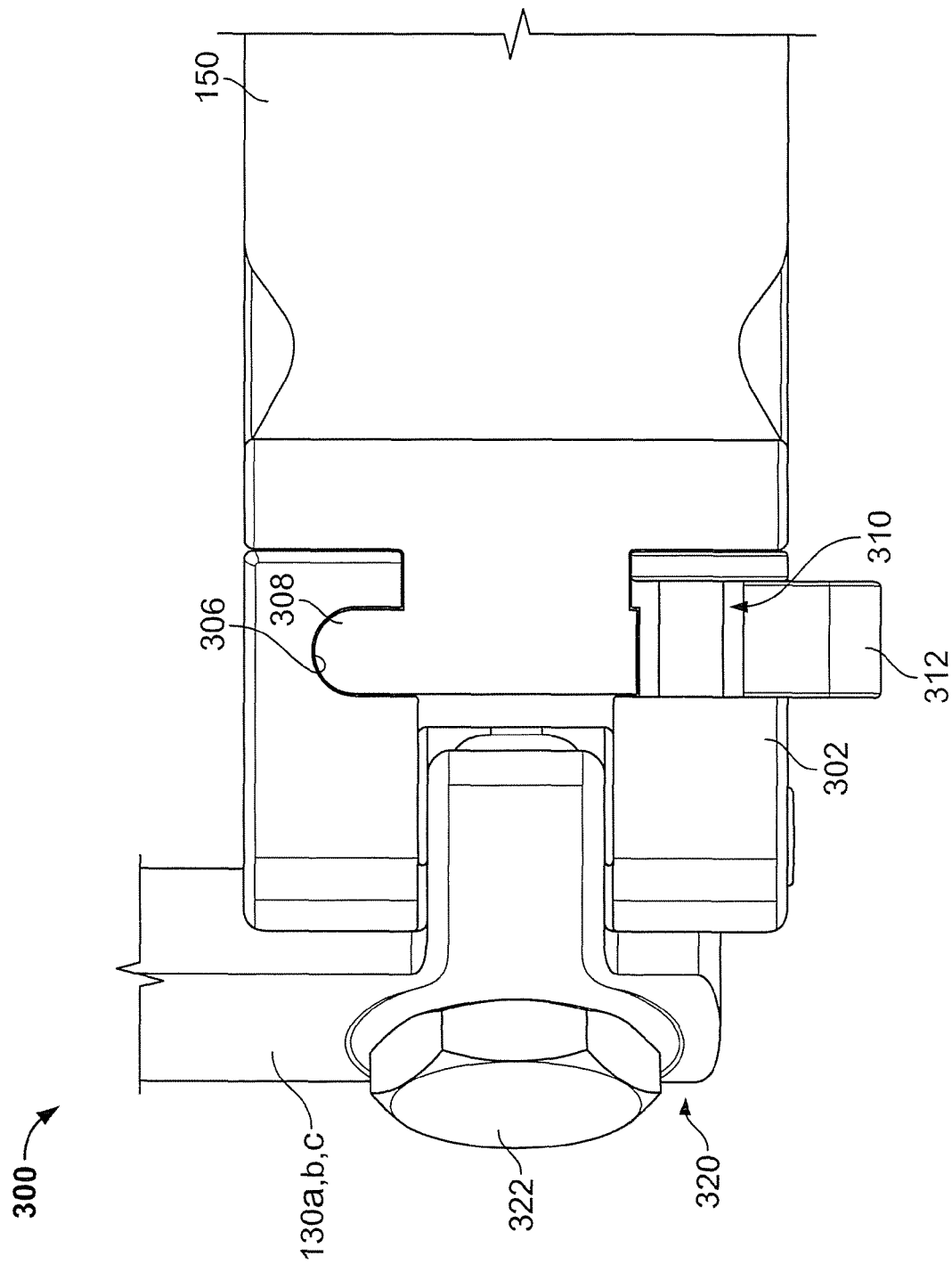
FIG. 8 is an enlarged sectional view of Detail C of FIG. 4.

The distal end of each of the first and second retractor arms 130a, 130b (generically referenced as 130) can be coupled to a blade angulator/connector 300, as illustrated in FIGS. 4, 6 and 8, for connecting a blade 150 to the retractor arm 130 in a quick-connect, self-locking manner. The blade angulator/connector 300 can include a blade holder 302 pivotably connected to the retractor arm 130 with a pivot element 304. The blade holder 302 can include a male or female quick-engagement formation 306 couplable with a conforming female or male quick-engagement formation 308 on the blade 150. The quick engagement formations 306, 308 can define a dovetail-type tongue-and-groove connection, for example, a pocket connection or other type of quick-connect/disconnect arrangement. The blade connector 300 can include a locking arm 310 biased to lock the blade 150 in the blade holder 302 in a self-locking manner. Pressing extension 312 of the locking arm 310 rotates the locking arm 310 to a release position that allows the blade 150 to be removed.

The blade connector 300 can also include a driver 320 that can control the rotation of the blade holder 302 and thereby the angulation or tilting of the blade 150 relative to the retractor arm 130. The driver 320 can include a head 322, a threaded portion 324 and a distal end 326. The driver 320 can be threaded through a threaded bore 132 of the retractor arm 130 such that the distal end 326 can engage a slot or groove or other channel 318 defined in the blade holder 302. The distal end 326 can be shaped to be rotatably and slidably received in the channel 318. The distal end 326 can have, for example a spherical or other bulbous shape. The driver 320 can be designed such that the driver 320 cannot be completely disengaged from the blade holder 302 during the full range of motion of the driver 320. Rotating the head 322 pivots the blade holder 302 and the attached blade 150 relative to the retractor arm 130, as shown in FIG. 7. Accordingly, the degree of angulation or tilting of the blade 150 can be continuously controlled and adjusted.

Figure 9A:
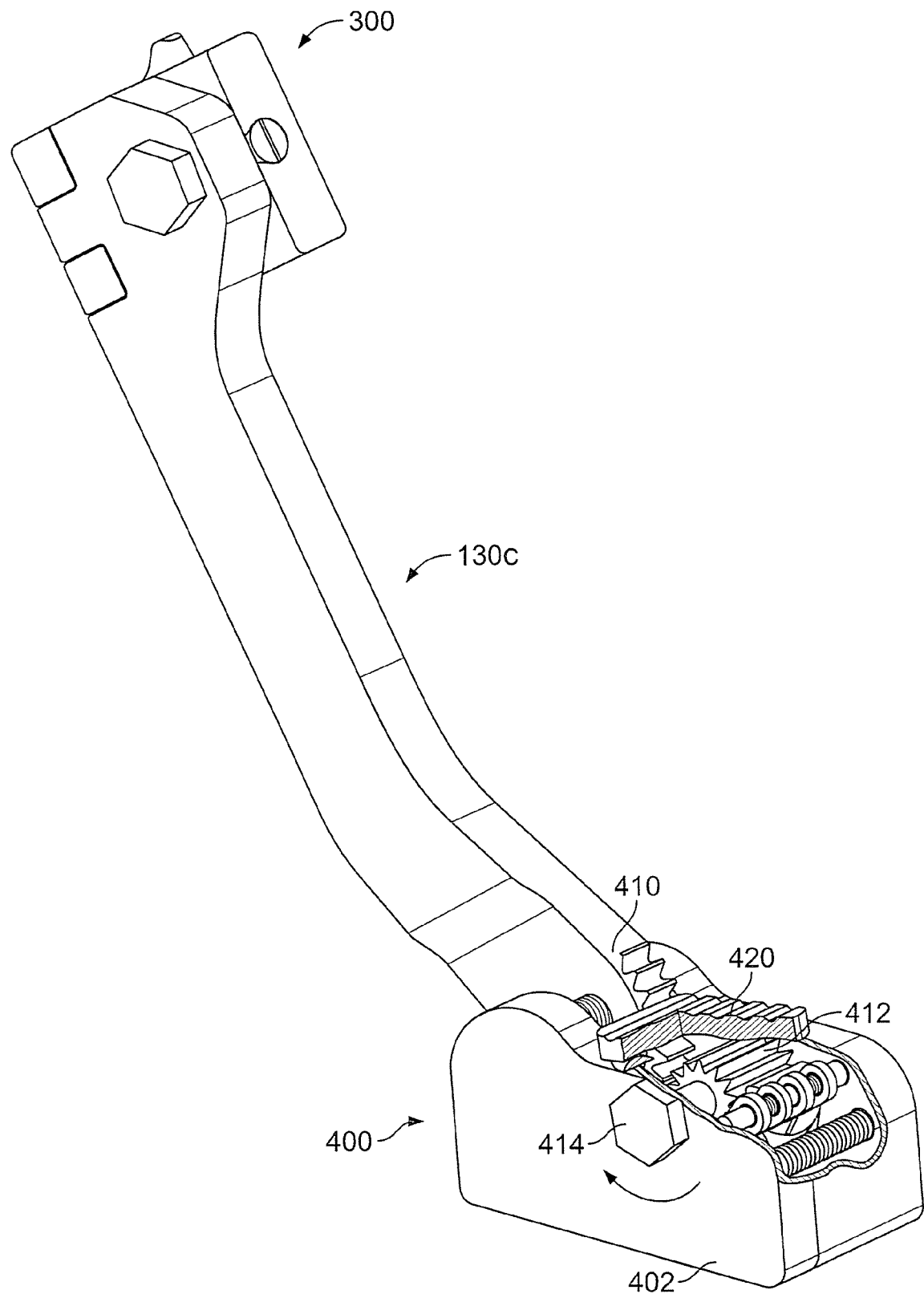
FIGS. 9A and 9B are perspective views of an exemplary retractor arm according to the present teachings, the modular arm shown with a partial cut-away view of one end.
Figure 9B:
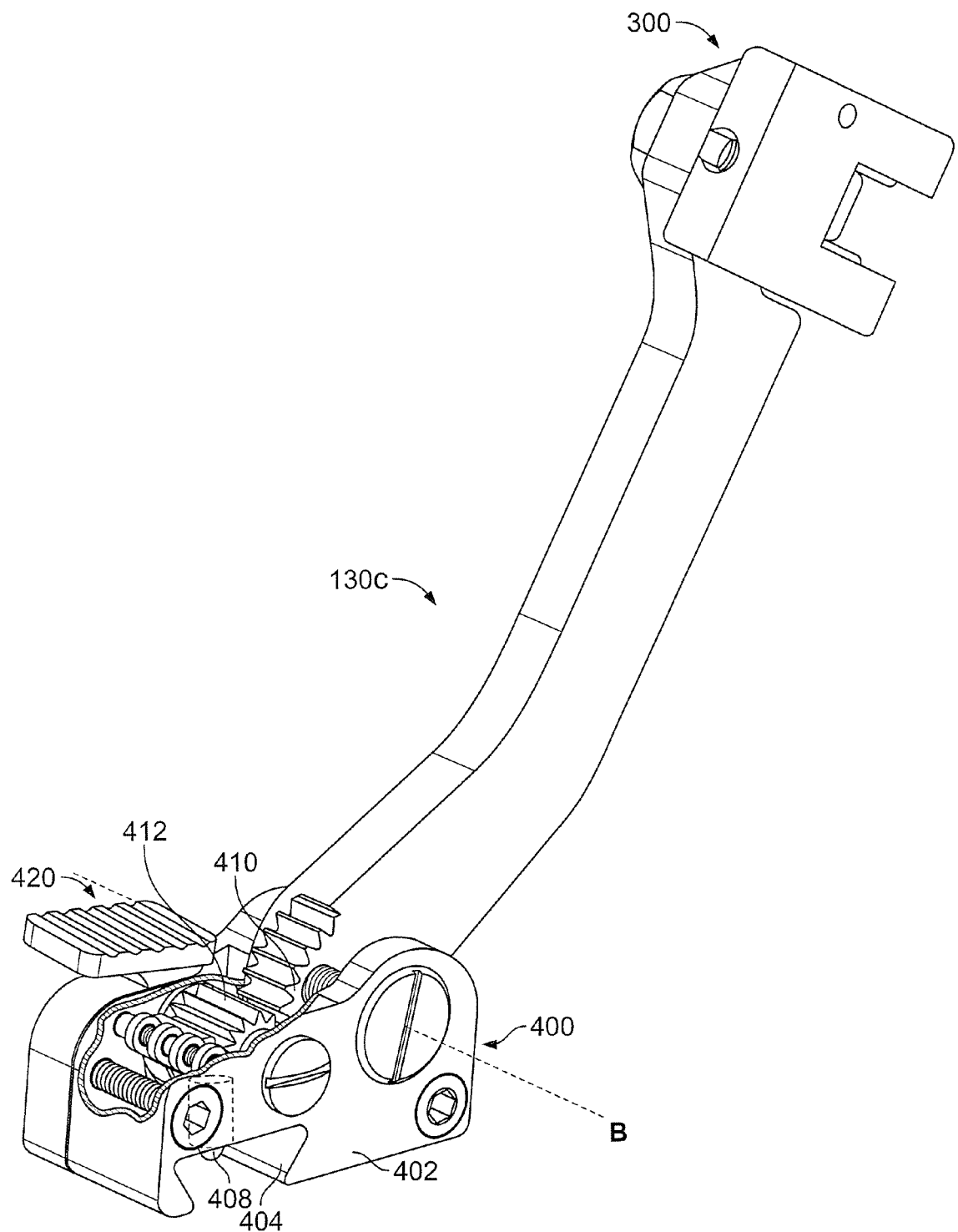

Referring to FIGS. 1, 9A and 9B, additional distraction can be provided as desired by connecting to the frame 101 multiple modular arms 130c. The modular arms 130c can be connected to the inner frame member 104 using a quick connect/disconnect arm connector 400. A blade connector, such as the blade connector 300 described above, can be used to connect the modular arm 130c to a blade 150 self-lockingly and with continuous adjustment control. The blade connector 300 can provide angulation that is independent for each blade 150 connected to the frame 101.

The arm connector 400 can allow each modular arm 130c to distract independently of any other modular arm 130c or retractor arm 130, 130a, 130b and can provide a self-locking and quick release connection. The arm connector 400 can include a modular housing 402 defining a quick-engagement formation 404 which can be engaged to a corresponding quick-engagement formation 406 on the frame 101 as shown in FIG. 7. The quick-engagement formations 404, 406 can be of the dovetail, pocket or quick-connect engagement type and can be self-locking. The exemplary arm connector 400 is shown, for example, with female/male dovetail formations 404, 406. A spring-loaded ball plunger 408 can be supported by the housing 402 to provide self-locking for the engagement formations 404, 406.

The modular arm 130c can include a gear 410 coupled to the housing 402 and engageable with a pinion 412 supported by the housing 402. A hex head or other actuating element 414 can be connected to the shaft of the pinion 412 to rotate the pinion. The pinion 412 can transfer rotational motion to the gear 410 and rotate the modular arm 130c about pivot axis B. Axis B is generally perpendicular to the frame pivot axis A. A trigger 420 can be activated to release a trigger lock that prevents rotational motion.

The retractor device 100 can be used with various arm combinations coupled to the frame 101. For example, FIG. 1 illustrates the frame 101 assembled with four blades 150. It will be appreciated that a smaller number of blades 150 or even a single blade 150 can be used with the frame 101. Similarly, more than four blades 150 can be used, if desired. The blades 150 can be curved or flat and can be of different widths, diameters, and lengths. Some blades 150 can define a blade channel that can be used to introduce a light source or a blade extension or a utility tool, such as a suction pump or other device.

The various components of the retractor device 100, including the outer and inner frame members 102, 104, the retractor arms 130a, 130b, the modular arms 130c, and the blades 150, can be made of metallic or polymeric materials. Polymer materials with radiolucent properties may be used when increased visibility is desirable.

The various control devices, including the frame driver 200, the distraction driver 250, the blade angulator/connector 300, and the arm connector 400, can be adjusted using a wrench, a detachable knob or other tool. The modular arms 130c can also be manually moved in the permissible rotational directions.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A surgical retractor comprising:
   a first frame member;
   a second frame member coupled to said first frame member and movable relative to said first frame member about a pivot axis from a first position nested with said first frame member to at least one second position disposed at an angle relative to said first frame member, the second frame member carrying at least one retractor arm;
   a first drive arrangement for driving said second frame member relative to said first frame member about said pivot axis; and
   a second drive arrangement operable to move said at least one retractor arm relative to said second frame member.

2. The surgical retractor of claim 1, wherein said second frame member is held in said first position and said second position relative to said first frame member by said first drive arrangement.

3. The surgical retractor of claim 1, wherein said second drive arrangement includes a pinion operable to engage a rack associated with said at least one retractor arm to selectively move said at least one retractor arm relative to said second frame member.

4. The surgical retractor of claim 1, wherein said at least one retractor arm includes two retractor arms and said second drive arrangement includes a pinion operable to engage a first rack associated with one of said two retractor arms and operable to engage a second rack associated with the other of said two retractor arms to move said retractor arms relative to said second frame member.

5. The surgical retractor of claim 1, wherein said at least one retractor arm translates in a direction substantially parallel to said pivot axis.

6. The surgical retractor of claim 1, further comprising a retractor blade coupled to said at least one retractor arm and movable with said at least one retractor arm relative to said second frame member.

7. The surgical retractor of claim 6, further comprising a third drive arrangement operable to adjust a position of said retractor blade relative to said at least one retractor arm.

8. The surgical retractor of claim 1, wherein said at least one second position includes a plurality of positions.

9. The surgical retractor of claim 1, wherein said second frame member is disposed in the same plane as said first frame member in said first position.

10. A surgical retractor comprising:
    a first frame member including a first cross member and a pair of first end portions extending from and substantially perpendicular to said first cross member;
    a second frame member rotatably coupled to said first frame member and including a second cross member and a pair of second end portions extending from and substantially perpendicular to said second cross member; and
    at least one retractor arm operably supported by said second frame member and movable relative to said second frame member between said pair of second end portions.

11. The surgical retractor of claim 10, wherein said second frame member is movable relative to said first frame member.

12. The surgical retractor of claim 10, further comprising a first drive arrangement operable to move said second frame member relative to said first frame member.

13. The surgical retractor of claim 12, wherein said second frame member is held in an adjusted position relative to said first frame member by said first drive arrangement.

14. The surgical retractor of claim 10, further comprising a second drive arrangement operable to move said at least one retractor arm relative to said second frame member.

15. The surgical retractor of claim 14, wherein said second drive arrangement includes a pinion operable to engage a rack associated with said at least one retractor arm to selectively move said at least one retractor arm relative to said second frame member.

16. The surgical retractor of claim 14, wherein said at least one retractor arm includes two retractor arms and said second drive arrangement includes a pinion operable to engage a first rack associated with one of said two retractor arms and operable to engage a second rack associated with the other of said two retractor arms to move said retractor arms relative to said second frame member.

17. The surgical retractor of claim 10, wherein said at least one retractor arm translates in a direction substantially parallel to said second cross member.

18. The surgical retractor of claim 10, further comprising a retractor blade coupled to said at least one retractor arm and movable with said at least one retractor arm relative to said second frame member.

19. The surgical retractor of claim 18, further comprising a third drive arrangement operable to adjust a position of said retractor blade relative to said at least one retractor arm.

20. The surgical retractor of claim 10, wherein at least one of said first cross member and said second cross member includes at least one of a convex or shaped surface to accommodate the human anatomy proximate to a surgical field.

21. A surgical retractor comprising:
    a first cross member;
    a pair of first end portions extending from and substantially perpendicular to said first cross member;
    a second cross member;
    a pair of second end portions extending from and substantially perpendicular to said second cross member, said pair of second end portions and said second cross member rotatably attached to said first cross member and said pair of first end portions;
    an opening defined substantially between said pair of first end portions;
    at least one retractor arm movably supported between said pair of first end portions and at least partially disposed within said opening; and
    at least one attachment feature extending away from said opening to support the surgical retractor relative to a surgical field.

22. The surgical retractor of claim 21, further comprising a first drive arrangement operable to move said second pair of end portions and said second cross member relative to said first pair of end portions and said first cross member.

23. The surgical retractor of claim 22, wherein said second pair of second end portions and said second cross member are held in an adjusted position relative to said first pair of end portions and said first cross member by said first drive arrangement.

24. The surgical retractor of claim 21, further comprising a second drive arrangement operable to move said at least one retractor arm relative to said first pair of end portions and said first cross member.

25. The surgical retractor of claim 24, wherein said second drive arrangement includes a pinion operable to engage a rack associated with said at least one retractor arm to selectively move said at least one retractor arm relative to said first pair of end portions and said first cross member.

26. The surgical retractor of claim 24, wherein said at least one retractor arm includes two retractor arms and said second drive arrangement includes a pinion operable to engage a first rack associated with one of said two retractor arms and operable to engage a second rack associated with the other of said two retractor arms to move said retractor arms relative to said first pair of end portions and said first cross member.

27. The surgical retractor of claim 21, wherein said at least one retractor arm translates in a direction substantially parallel to said first cross member.

28. The surgical retractor of claim 21, further comprising a retractor blade coupled to said at least one retractor arm and movable with said at least one retractor arm relative to said first pair of end portions and said first cross member.

29. The surgical retractor of claim 28, further comprising a third drive arrangement operable to adjust a position of said retractor blade relative to said at least one retractor arm.

30. A surgical retractor comprising:
a first cross member;
a pair of first end portions extending from and substantially perpendicular to said first cross member;
an opening defined substantially between said pair of first end portions;
at least one retractor arm at least partially disposed within said opening;
at least one attachment feature extending away from said opening and substantially perpendicular to said first cross member to support the surgical retractor relative to a surgical field;
a second cross member; and
a pair of second end portions extending from and substantially perpendicular to said second cross member and rotatably attached to said first cross member and said first pair of first end portions.

31. The surgical retractor of claim 30, wherein said pair of second end portions are rotatably attached to said first pair of first end portions.

32. The surgical retractor of claim 30, wherein said at least one retractor arm is movably supported between said pair of first end portions.

33. A surgical retractor comprising:
a first frame member;
a second frame member coupled to said first frame member and movable relative to said first frame member about a pivot axis from a first position nested with said first frame member to at least one second position disposed at an angle relative to said first frame member, the second frame member carrying at least one retractor arm; and
a first drive arrangement for driving said second frame member relative to said first frame member about said pivot axis;
wherein said at least one retractor arm translates in a direction substantially parallel to said pivot axis.

34. A surgical retractor comprising:
a first frame member;
a second frame member coupled to said first frame member and movable relative to said first frame member about a pivot axis from a first position nested with said first frame member to at least one second position disposed at an angle relative to said first frame member, the second frame member carrying at least one retractor arm;
a first drive arrangement for driving said second frame member relative to said first frame member about said pivot axis; and
a retractor blade coupled to said at least one retractor arm and movable with said at least one retractor arm relative to said second frame member.

35. A surgical retractor comprising:
a first frame member including a first cross member and a pair of first end portions extending from and substantially perpendicular to said first cross member;
a second frame member coupled to said first frame member and including a second cross member and a pair of second end portions extending from and substantially perpendicular to said second cross member;
at least one retractor arm operably supported by said second frame member and movable relative to said second frame member between said pair of second end portions; and
a first drive member operable to move said second frame member relative to said first frame member.

36. A surgical retractor comprising:
a first frame member including a first cross member and a pair of first end portions extending from and substantially perpendicular to said first cross member; and
a second frame member coupled to said first frame member and including a second cross member and a pair of second end portions extending from and substantially perpendicular to said second cross member;
wherein at least one of said first cross member and said second cross member includes at least one of a convex or shaped surface to accommodate the human anatomy proximate to a surgical field.

37. The surgical retractor of claim 36, further comprising at least one retractor arm operably supported by said second frame member and movable relative to said second frame member between said pair of second end portions.

* * * * *

UNITED STATES PATENT AND TRADEMARK OFFICE
CERTIFICATE OF CORRECTION

| | | |
|---|---|---|
| PATENT NO. | : 7,931,589 B2 | Page 1 of 1 |
| APPLICATION NO. | : 11/558095 | |
| DATED | : April 26, 2011 | |
| INVENTOR(S) | : Dan S. Cohen et al. | |

It is certified that error appears in the above-identified patent and that said Letters Patent is hereby corrected as shown below:

Col. 1, Line 64 - "an distraction" should be --a distraction--.

Col. 3, Line 31 - "by a moving" should be --by moving--.

Signed and Sealed this
Fifth Day of July, 2011

David J. Kappos
*Director of the United States Patent and Trademark Office*